(12) United States Patent
Klein et al.

(10) Patent No.: US 11,844,899 B2
(45) Date of Patent: *Dec. 19, 2023

(54) VIRTUAL RESPIRATORY GAS DELIVERY SYSTEMS AND CIRCUITS

(71) Applicant: THORNHILL SCIENTIFIC INC., North York (CA)

(72) Inventors: Michael Klein, Toronto (CA); Joseph Fisher, Thornhill (CA)

(73) Assignee: THORNHILL SCIENTIFIC INC., North York (CA)

(*) Notice: Subject to any disclaimer, the term of this patent is extended or adjusted under 35 U.S.C. 154(b) by 376 days.

This patent is subject to a terminal disclaimer.

(21) Appl. No.: 17/124,805

(22) Filed: Dec. 17, 2020

(65) Prior Publication Data

US 2021/0138171 A1 May 13, 2021

Related U.S. Application Data

(63) Continuation of application No. 15/789,605, filed on Oct. 20, 2017, now Pat. No. 10,974,001, which is a
(Continued)

(51) Int. Cl.
*A61M 16/00* (2006.01)
*A61M 16/08* (2006.01)
(Continued)

(52) U.S. Cl.
CPC .... *A61M 16/0069* (2014.02); *A61M 16/0003* (2014.02); *A61M 16/026* (2017.08); *A61M 16/0891* (2014.02); *A61M 16/12* (2013.01); *A61M 16/122* (2014.02); *A61B 5/091* (2013.01); *A61M 16/01* (2013.01); *A61M 16/204* (2014.02);
(Continued)

(58) Field of Classification Search
CPC ............ A61M 16/0069; A61M 16/122; A61M 16/003; A61M 16/0891; A61M 16/0051; A61M 16/12; A61M 16/204; A61M 16/01; A61B 5/091

See application file for complete search history.

(56) References Cited

U.S. PATENT DOCUMENTS

| 5,404,871 A | 4/1995 | Goodman et al. |
| 5,918,596 A | 7/1999 | Heinonen |

(Continued)

FOREIGN PATENT DOCUMENTS

| CN | 1809395 A | 7/2006 |
| CN | 101547716 A | 9/2009 |

(Continued)

OTHER PUBLICATIONS

EPO. Communication pursuant to Article 94(3) EPC, dated Mar. 3, 2017, re European Patent Application No. 13764140.3.
(Continued)

*Primary Examiner* — Margaret M Luarca
(74) *Attorney, Agent, or Firm* — Perry + Currier Inc.

(57) ABSTRACT

A respiratory gas delivery system monitors gas flow over the course of a breath in real time and uses this parameter to simulate, in whole or part, the function of a reference respiratory gas delivery system, in particular structural features, particularly structural components of parts of the reference system, to overcome a structural limitation of the reference system.

10 Claims, 5 Drawing Sheets

Related U.S. Application Data continuation of application No. 14/386,752, filed as application No. PCT/CA2013/000266 on Mar. 19, 2013, now abandoned.

(60) Provisional application No. 61/612,791, filed on Mar. 19, 2012.

(51) Int. Cl.
*A61M 16/12* (2006.01)
*A61M 16/20* (2006.01)
*A61B 5/091* (2006.01)
*A61M 16/01* (2006.01)

(52) U.S. Cl.
CPC ............ *A61M 2016/0027* (2013.01); *A61M 2016/0039* (2013.01); *A61M 2202/02* (2013.01); *A61M 2202/0225* (2013.01); *A61M 2202/0283* (2013.01); *A61M 2205/3334* (2013.01); *A61M 2205/50* (2013.01); *A61M 2205/502* (2013.01); *A61M 2230/432* (2013.01)

(56) References Cited

U.S. PATENT DOCUMENTS

| | | | |
|---|---|---|---|
| 6,089,229 | A | 7/2000 | Bathe et al. |
| 7,861,717 | B1 | 1/2011 | Krebs |
| 2002/0185129 | A1 | 12/2002 | Fisher et al. |
| 2003/0015196 | A1 | 1/2003 | Hodges et al. |
| 2006/0207594 | A1 | 9/2006 | Stenzler et al. |
| 2007/0062531 | A1 | 3/2007 | Fisher et al. |
| 2007/0062534 | A1 | 3/2007 | Fisher et al. |
| 2012/0180790 | A1 | 7/2012 | Montgomery et al. |
| 2012/0215124 | A1 | 8/2012 | Fisher et al. |
| 2013/0179761 | A1 | 7/2013 | Cho et al. |
| 2014/0282399 | A1 | 9/2014 | Gorelik et al. |

FOREIGN PATENT DOCUMENTS

| | | |
|---|---|---|
| CN | 201692453 U | 1/2011 |
| CN | 102107037 A | 6/2011 |
| EP | 0977609 A1 | 2/2000 |
| WO | WO-9909388 A2 | 2/1999 |
| WO | WO-2007012197 A1 | 2/2007 |
| WO | WO-2011134546 A1 | 11/2011 |
| WO | WO-2011143751 A1 | 11/2011 |
| WO | WO-2012139204 A1 | 10/2012 |
| WO | WO-2013082703 A1 | 6/2013 |
| WO | WO-2013163735 A1 | 11/2013 |

OTHER PUBLICATIONS

EPO, Communication pursuant to Article 94(3) EPC, dated Jan. 18, 2019, re European Patent Application No. 13764140.3.
EPO, Extended European Search Report, dated Mar. 21, 2016, re European Patent Application No. 13764140.3.
CIPO, Examination Report, dated Mar. 7, 2019, re Canadian Patent Application No. 2867745.
USPTO, Non-Final Rejection, dated Oct. 18, 2019, re U.S. Appl. No. 15/789,605.
CNIPA, First Office Action, dated Dec. 1, 2015, re Chinese Patent Application No. 201380026287.9.
EPO, Communication pursuant to Article 94(3) EPC, dated Jun. 26, 2018, re European Patent Application No. 13764140.3.
EPO, Supplementary European Search Report, dated Oct. 8, 2015, re European Patent Application No. 13764140.3.
ISA/CA, International Search Report and Written Opinion, dated Jul. 8, 2013, re PCT International Patent Application No. PCT/CA2013/000266.
WIPO/IB, International Preliminary Report on Patentability (Ch.1), dated Oct. 2, 2014, re PCT International Patent Application No. PCT/CA2013/000266.

VIRTUAL RESPIRATORY GAS DELIVERY SYSTEMS AND CIRCUITS

FIELD OF THE INVENTION

The present invention relates to a respiratory gas delivery system that monitors at least one parameter over the course of a breath in real time for example gas flow and uses the parameter to simulate, in whole or part, the function of a reference respiratory gas delivery system, according to one aspect, to simulate features, for example, structural features, particularly structural components of parts (for example tubing, valves and reservoirs) of the reference system, for example, to overcome a structural limitation of the reference system, in particular, at least one structural feature of a reference breathing circuit adapted for use with or forming part of the reference gas delivery system.

BACKGROUND OF THE INVENTION

In many clinical and research situations, a subject is required to breathe through a breathing circuit. These circuits are normally designed to deliver different compositions of gases at different points throughout the breath cycle. In many cases, the breathing circuits are designed to minimize the use of an expensive component gas of the breathing mixture. These circuits, however, are normally designed with, and constructed from, components such as tubing, reservoir bags, and valves. These components are expensive, bulky, and prone to failure.

For example, the Hi-Ox 80 (CareFusion) breathing circuit is a breathing circuit designed to provide high inspired fractions of oxygen while minimizing the flow rate of oxygen to the patient. In this circuit, a constant flow rate of oxygen is provided to the circuit, the oxygen accumulating in a reservoir. The patient inspires through two one-way valves in parallel. The inlet side of the oxygen one-way valve is connected to the oxygen reservoir, while the inlet side of the air one-way valve is open to the atmosphere. The oxygen-supply one-way valve has negligible cracking pressure and so opens for any inspiratory effort. The air-supply one-way valve has a small cracking pressure which causes it to open only when a negative pressure is generated in the breathing circuit. In this way, during a typical inspiration, the patient inspires oxygen from the oxygen reservoir first. When the reservoir is empty, continued inspiration generates a negative pressure in the circuit thereby opening the air-supply one-way valve. Therefore, the balance of the breath is drawn from ambient air. Expiration is directed to the ambient atmosphere through a third expiratory one-way valve.

While this circuit is effective, it has a number of limitations. Firstly, the mechanical components are prone to failure. Failure of the one-way valves, such as a failure of the oxygen-supply one-way valve to open, may cause the subject to breath only ambient atmospheric air. Failure of the air-supply one-way valve to open will limit the subject's minute ventilation to the flow rate of oxygen to the circuit. On the other hand, if the oxygen-supply one-way valve does not effectively prevent back flow, the subject may expire into, and rebreathe from, the oxygen reservoir. Secondly, in addition to potential failures, the one-way valves increase the resistance to flow in the breathing circuit thereby increasing the work of breathing. This is uncomfortable for most patients, and may be a significant limitation to use in elderly patients or those with pulmonary disease. Thirdly, the size of the manifold which houses all the valves together with the reservoir can be quite large and cumbersome for some situations. For example, in an emergency medical resuscitation situation where access is required to the subject's chest, the oxygen reservoir may be in the way. Here, the physicians must remove the breathing circuit to access the chest.

SUMMARY OF THE INVENTION

According to one aspect, the invention is directed to a respiratory gas delivery system adapted to deliver an inspiratory gas of variable composition comprising:
A. a gas delivery apparatus operatively connected to a processor:
B. a flow sensor adapted to monitor in real time the rate of inspiration of a gas;
wherein, for a plurality of respective inspiratory cycles $[i]_1$ to $[i]_n$ and a plurality of time points $[t]_1$ to $[t]_n$, over the course of a respective inspiratory cycle $[i]$, the processor is configured to:
(a) use output from the flow sensor to monitor the cumulative volume of gas inspired in the respective inspiratory cycle at any given time point $[t]_1$ to $[t]_n$;
(b) execute an algorithm to determine a desired composition of the inspired gas based on whether or not at least one threshold cumulative volume of a desired gas composition has been inspired in the respective inspiratory cycle, the desired composition including a composition selected from a first composition selected for delivery for a first portion of a breath and at least one alternate nth composition; and
(c) generate a control signal effective to signal the gas delivery apparatus to deliver the first composition in the first part of breath and the nth composition during the course of a breath based on whether or not the at least one threshold cumulative volume has been reached.

Optionally, the first composition corresponding to a first portion of a breath is determined using at least one first criterion and the at least one alternate nth composition is determined using at least one different criterion.

Optionally, the at least one pre-determined cumulative volume is set to be less than a subject's tidal volume minus anatomic dead space volume such that the entire volume of the first composition is destined to enter a subject's alveolar space.

Optionally, the alternate composition is a neutral gas.

Optionally, the alternative composition is a percentage composition of a constituent gas as low as 0%, wherein the constituent gas is of a type determined by a user to warrant conservation by reducing delivery to the anatomical dead space.

Optionally, a threshold cumulative volume for a respective breath $[i]$ may be set to deliver a target total inspiratory volume of a first gas composition over a series of inspiratory cycles $[i]_1$ to $[i]_n$.

By way of example only, n may be 7 and the series may include a current inspiratory cycle $[i]$. Delivering 500 ml of a gas over 7 breaths: If after 6 breaths, 470 ml of the gas has been delivered, in the $7^{th}$ breath the threshold volume is computed and set to be 30 m.

Optionally, the processor is configured to simulate gas delivery from at least a virtual first gas reservoir and a second gas source, optionally a virtual second gas reservoir, wherein:
(a) the first gas reservoir and the second gas source e.g. gas reservoir contain a gas of at least specifiable or specified composition;

(b) at least the first gas reservoir is assumed to contain a gas corresponding to a first portion of a breath, the processor configured to send a control signal to signal to the gas delivery apparatus to deliver a gas of a specified composition of the first gas reservoir for the first part of a respective inspiratory cycle [i], the first gas reservoir set to contain a volume of gas adapted to be depleted in each inspiratory cycle at a reservoir specific depletion rate which tracks the inspiratory flow rate measured by the flow sensor, and (c) the processor generates a control signal effective to signal the gas delivery apparatus to deliver a gas of composition substantially equal to the specifiable or specified composition of the at least second gas reservoir for a second part of a respective inspiratory cycle [i] when the first gas reservoir is depleted.

Optionally, the volume of the at least first gas reservoir is set based on an assumption that the first gas reservoir is continually filled with a gas of a specified composition at a specifiable or specified reservoir-specific fill rate which is less than the reservoir specific depletion rate.

Optionally, the volume of the at least first gas reservoir is set based on an assumption that the first gas reservoir is full at the start of an inspiratory cycle, the volume selected to be a volume that can be predicted to be depleted at a reservoir specific depletion rate which tracks the inspiratory flow rate measured by the flow sensor.

Optionally, the apparatus is configured to deliver a first gas of a first composition for a first part of each inspiratory cycle [i] and a second gas of a second composition for a second part of each inspiratory cycle [i].

Optionally, the apparatus is configured to simulate gas delivery from two gas sources e.g. gas reservoirs, wherein the first gas source e.g. reservoir is exclusively depleted in a first part of each inspiratory cycle [i], and the second gas source e.g. reservoir is exclusively delivered in a second part of each inspiratory cycle [i]. The second gas source e.g. gas reservoir is optionally associated with a parameter such as volume or fill rate, however especially if the second gas source is set to have no volume limit, for example where the second gas source is drawn upon for the remainder of any given inspiratory cycle, whether or not it is depleted may be moot.

Optionally, the fill rate of the first reservoir is less than the subject's total inspired volume minus the total volume of gas inspired into the anatomic dead space volume over a measurement interval.

Optionally, the measurement interval is one minute.

Optionally, the composition of gas delivered in the second part of each inspiratory cycle [i] is neutral with respect to at least one constituent gas of the inspiratory gas.

According to another aspect, the invention is directed to a computer program product or a programmable IC chip comprising program code for controlling a gas delivery apparatus which is adapted to deliver an inspiratory gas of variable composition comprising:

Program code for obtaining input from a flow sensor adapted to monitor in real time the rate of inspiration of a gas;

Program code for configuring a processor, for a plurality of respective inspiratory cycles $[i]^1$ to $[i]^n$, throughout each inspiratory cycle [i], to (a) use output from the flow sensor to monitor the volume of inspired gas in the respective inspiratory cycle; (b) execute an algorithm to compute, specify or obtain input of a desired composition of the inspired gas using as input at least the cumulative volume of inspired gas in the respective inspiratory cycle;

(c) generate a control signal effective to signal the gas delivery apparatus to deliver a gas of composition substantially equal to the computed composition.

Optionally, the program code configures the processor to simulate gas delivery from a plurality of gas reservoirs, wherein:

(a) each reservoir contains a gas of specifiable or specified composition;

(b) at least one reservoir (the one containing gas adapted to be delivered in a first portion of a breath), optionally each reservoir, is continually filled with a gas of the associated composition at a specifiable or specified reservoir specific fill rate;

(c) at least the one and optionally each reservoir is continually depleted at a specifiable reservoir specific depletion rate. Optionally, the sum of the individual depletion rates equal to the inspiratory flow rate measured by the flow sensor;

(d) wherein the program code configures the processor to generate a control signal effective to signal the gas delivery apparatus to deliver a gas of composition substantially equal to a blend of the reservoir gases weighted by their associated depletion rates.

Where a depletion rate is specified only for the gas reservoir containing a gas adapted to be delivered in a first portion of a breath the second reservoir may assumed never to be depleted, depleted over a time course corresponding to the duration of the remainder of a cycle of inspiration or depleted after consumption of a particular constituent gas over a period of use. Hence this model may be interchangeable with a model in which only one reservoir is present and depleted, the at least one gas of an alternative composition delivered only the remaining portion of an inspiratory cycle.

Optionally, the patient is a spontaneously breathing patient. Depletion of at least the first delivered gas represents an embodiment of an algorithm adapted to send a control signal to signal the gas delivery apparatus to deliver a gas of second composition which is specifiable or specified based on a different criteria which demarcates a juncture at or preceding the juncture at which inspired gas has already filled the alveoli and begins to fill the anatomical dead space, Accounting for the fact that some not all of an inspired gas will enter a subject's alveolar space is useful for a variety of purposes including enabling an expensive gas to be conserved or enabling a neutral gas or air to be delivered in each inspiratory cycle.

Optionally, the program code adapts the apparatus to deliver a first gas of a first composition for a first part of each inspiratory cycle [i] and a second gas of a second composition for a second part of each inspiratory cycle [i].

Optionally, the program code adapts the apparatus to simulate gas delivery from two gas reservoirs, wherein the first reservoir is exclusively depleted in a first part of a each inspiratory cycle [i], and the second reservoir is exclusively delivered in a second part of each inspiratory cycle [i].

Optionally, the fill rate of the first reservoir is less than the subject's total inspired volume minus the total volume of gas inspired into the anatomic dead space volume over a measurement interval.

Optionally, the measurement interval is one minute.

Optionally, the composition of gas delivered in the second part of each inspiratory cycle [i] is neutral with respect to at least one constituent gas of the inspiratory gas.

According to one aspect, the invention is directed to a method using a gas delivery apparatus for delivering an inspiratory gas of variable composition and a computer program product or programmable IC chip adapted to implement the method, the gas delivery apparatus operatively connected to a processor, comprising A. obtaining output from a flow sensor adapted to monitor in real time the rate of inspiration of a gas;
B. using output from the flow sensor to monitor the cumulative volume of gas inspired in the respective inspiratory cycle at any given time point $[t]_1$ to $[t]_n$ over the course of a respective inspiratory cycle [i];
C. executing an algorithm to determine a desired composition of the inspired gas based on whether or not at least one threshold cumulative volume of a gas composition has been inspired in the respective inspiratory cycle, the desired composition including a composition selected from a first composition corresponding to a first portion of a breath and at least one alternate nth composition;
D. generating a control signal effective to signal the gas delivery apparatus to deliver the first composition in the first part of a respective inspiratory cycle [i] and at least one alternate nth composition during the course of the inspiratory cycle based on whether or not the at least one pre-determined threshold cumulative volume has been reached.

Optionally, the composition corresponding to a first portion of a inspiratory cycle is determined using at least one first criterion and wherein the at least one alternate composition is determined using at least one different criterion.

Optionally, the at least one pre-determined cumulative volume is set to be less than a subject's tidal volume minus anatomic dead space volume such that the entire volume of the composition corresponding to a first portion of a inspiratory cycle is destined to enter a subject's alveolar space.

Optionally, the alternative composition is a neutral gas.

Optionally, the alternative composition is a percentage composition of a constituent gas as low as 0%, wherein the constituent gas is of a typo determined by a user to warrant conservation by reducing delivery to the anatomical dead space.

Optionally, the method and the computer program product simulate gas delivery from at least a virtual first gas reservoir and a virtual second gas reservoir, wherein:
(a) the first gas reservoir and the second gas reservoir contain a gas of specifiable or specified composition;
(b) at least the first gas reservoir is assumed to contain a gas corresponding to a first portion of a inspiratory cycle, the method comprising sending a control signal to signal to the gas delivery apparatus to deliver a gas of a specified composition of the first gas reservoir for the first part of a respective inspiratory cycle [i], the first gas reservoir programmed to contain a volume of gas adapted to be depleted in each inspiratory cycle at a reservoir specific depletion rate which tracks the inspiratory flow rate measured by the flow sensor;
(c) generating a control signal effective to signal the gas delivery apparatus to deliver a gas of composition substantially equal to the specifiable or specified composition of the at least second gas reservoir for a second part of a respective inspiratory cycle [i] when the first gas reservoir is depleted.

To carry out the method, the computer program product includes program code which specifies or enables specification of the composition of the first gas reservoir and the second gas reservoir, program code for sending a control signal to signal to the gas delivery apparatus to deliver a gas of a specified composition of the first gas reservoir for the first part of a respective inspiratory cycle [i]; program code for specifying the volume and/or fill rate of the first gas reservoir, wherein the first gas reservoir contains a volume of gas adapted to be depleted in each inspiratory cycle at a reservoir specific depletion rate which tracks the inspiratory flow rate measured by the flow sensor; and program code for generating a control signal effective to signal the gas delivery apparatus to deliver a gas of composition substantially equal to the specified composition of the at least second gas reservoir for a second part of a respective inspiratory cycle [i] when the first gas reservoir is depleted.

Optionally, the volume of the at least first gas reservoir is set based on an assumption that the first gas reservoir is continually filled with a gas of an associated composition at a specifiable or specified reservoir-specific fill rate which is less than the reservoir specific depletion rate.

Optionally, the volume of the at least first gas reservoir is set based on an assumption that the first gas reservoir is full at the start of an inspiratory cycle, the volume selected a volume that can be predicted to be depleted the reservoir specific depletion rate which tracks the inspiratory flow rate measured by the flow sensor.

Optionally, the method is adapted to deliver a first gas of a first composition for a first part of each inspiratory cycle [i] and a second gas of a second composition for a second part of each inspiratory cycle [i].

Optionally, the method is adapted to simulate gas delivery from two gas reservoirs, wherein the first reservoir is exclusively depleted in a first part of each inspiratory cycle [i], and the second reservoir is exclusively drawn upon e.g. depleted in a second part of each inspiratory cycle [i].

Optionally, the fill rate of the first reservoir is less than the subject's total inspired volume minus the total volume of gas inspired into the anatomic dead space volume over a measurement interval.

Optionally, the measurement interval is one minute.

Optionally, the composition of gas delivered in the second part of each inspiratory cycle [i] is neutral with respect to at least one constituent gas of the inspiratory gas.

Optionally, the cumulative volume in a respective inspiratory cycle [I] is computed to achieve a target total inspiratory volume of a gas of a first gas composition over a series of inspiratory cycles, the series optionally at least including the current inspiratory cycle [i].

For example, if a volume X (e.g. 500 ml) is set to be delivered over Y inspiratory cycles (e.g. 7 inspiratory cycles), the processor is programmed, e.g. after (Y−1) inspiratory cycles have delivered a volume Z (e.g. 470 ml of the gas) to compute the threshold volume for the last inspiratory cycle to be X-Z (i.e. 30 ml.).

According to one aspect, the invention is directed to a respiratory gas delivery system adapted to deliver an inspiratory gas of variable composition comprising:
A. a gas delivery apparatus operatively connected to a processor;
B. at least one device adapted to monitor at least one condition representing a juncture in a respective inspiratory cycle [i] which satisfies at least one the following criteria:
a) a specifiable or specified volume of a desired gas composition has already been inspired in the respective inspiratory cycle;
b) a specifiable or specified amount of at least one constituent gas X has been inspired in the respective inspiratory cycle;

c) a volume of gas yet to be inspired in the respective inspiratory cycle exceeds a subject's anatomical dead space volume;

wherein, for a plurality of respective inspiratory cycles $[i]_1$ to $[i]_n$ the processor is configured to:

(a) use output from the at least one device to monitor the at least one condition based on the at least one criteria;

(b) execute an algorithm to determine a desired composition of the inspired gas based on whether or not the condition is satisfied, the desired composition including a composition selected from a first composition selected for delivery for a first portion of a inspiratory cycle and at least one alternate nth composition;

(c) generate a control signal effective to signal the gas delivery apparatus to deliver the first composition during a first portion of an inspiratory cycle at least one alternate composition during the course of a inspiratory cycle based on whether the condition is satisfied.

The device may include at least one of a measurement device such as a flow sensor, gas analyzer or a pressure sensor, a device adapted to control the tidal volume of a subject (e.g. a ventilator), a subject operated input device or a prompting device. A subject operated input device may be of any time in which enables a subject to signify the commencement of an end of an inspiratory cycle (i.e. winding down of the subject's inspiratory effort). A prompting device may include a device which enables a subject to readily target a value within range of values of a parameter that is correlated to volume of or duration of an inspiratory effort. Optionally, the system includes at least one measurement device that monitors in real time the cumulative volume of gas inspired in at least a first portion of an inspiratory cycle. Optionally, the system includes at least one measurement device that monitors in real time the pressure in a patient airway interface or conduit leading to patient airway interface, for example to monitor the progression, commencement and/or completion of an inspiratory and/or expiratory effort. Optionally, the system includes at least one measurement device that monitors in real time the concentration of at least one constituent gas.

According to one embodiment, the invention is directed to simulating a breathing circuit of a respiratory gas delivery system (a reference circuit and a reference system) using an alternative system so that the gas delivered to the patient—at least one of flow and composition—is substantially the same when using the alternate system and the reference circuit (i.e. with respect to a given output—flow or composition or both—the two circuits are functionally interchangeable at least in the sense that the alternate system performs the function of the reference system, albeit, optionally, in at least one respect, in a relatively advantageous manner. For example, the alternative system may be safer (e.g. less prone to failure), more robust, less bulky from the standpoint of making caregiver access to the patient easier, etc.

Functional equivalence, in term of flow, means that the pattern of flow. In at least one aspect, this alternate system of the invention virtualizes components of the reference breathing circuit in the sense that a control algorithm of the alternative system supplants structural features (e.g. at least one structural component) of the reference circuit, for example, a physical gas reservoir with an accumulator in computer memory.

Thus, according to one aspect, the invention is directed to a respiratory gas delivery system adapted for use with a first breathing circuit, the first breathing circuit optionally having at least one gas conduit leading to a patient airway interface, characterized in that the respiratory gas delivery system virtualizes at least one structural feature, optionally at least one structural component, optionally at least one set of structural parts of a reference, second breathing circuit, the respiratory gas delivery system including:

a) at least one device adapted for selecting a juncture during an inspiratory cycle for switching between a first gas composition and at least one alternate, nth gas composition, optionally a juncture that demarcates a juncture preceding a point at which inspired gas has already fined the alveoli and begins to fill the anatomical dead space, optionally a juncture identified by monitoring at least one parameter in real time, optionally a parameter selected from at least one of volume, pressure and gas concentration, optionally volume, optionally a flow sensor, positioned in relation to the first breathing circuit, for at least determining the volume gas inhaled via the patient airway interface;

b) a gas delivery apparatus for delivering a gas comprising a plurality of component or constituent gases into the patient airway interface, the gas delivery apparatus operatively connected to a computer, and optionally c) a gas analyzer for analyzing the gas concentration of one or more gases inhaled and/or exhaled by the subject;

wherein the computer is optionally configured to supplant the at least structural component, optionally at least one set of structural parts of the reference breathing circuit, the set of structural parts optionally including at least one part selected from a gas reservoir, a valve and a conduit, by using at least one of an algorithmic and a mathematical model of the at least one set of structural parts to generate gas delivery characteristics that simulate the functions of said set of structural parts. Optionally, the at least one set of structural parts simulated by a respiratory gas delivery system according to the invention comprises or consists of a set of structural parts adapted to direct gas flow from a first circuit flow path, optionally adapted to be open at the start of each inspiratory cycle, to at least one alternate, nth (e.g. second) circuit flow path during the course of a given inspiratory cycle. Optionally, the first circuit flow path is adapted to provide a gas of a first gas composition and the at least one alternate flow path is adapted to provide gas of at least one alternate nth gas composition. Optionally the first circuit flow path is operatively connected to a first gas source (the system simulates gas flow characteristics of the first gas source, optionally a maximum volume or rate of flow and/or a composition) optionally a first gas reservoir and the respiratory gas delivery system of the invention simulates cyclical replenishment and depletion of at least first gas reservoir. Optionally, the at least one alternate nth circuit flow path of the reference breathing circuit is a second gas source and the system of the invention simulates the gas flow characteristics of at least one second gas source, optionally the composition of the at least one second gas source. Optionally, the at least one second gas source is a reservoir, optionally a reservoir that holds a subject's exhaled gas, the at least one alternate circuit flow path of the reference breathing circuit optionally adapted to delver the subjects last expired gas from the immediately preceding breath first.

According to one embodiment, the respiratory gas delivery system of the invention accounts for how the supplanted component(s) of a reference breathing circuit work within a reference respiratory gas delivery system which the system of the invention simulates qualitatively and/or quantitatively, for example so that the respiratory gas delivery system of the invention is functionally equivalent (able to perform the same functions), to the extent desired (a system of the invention can be considered to function equivalently to a reference system if it performs the same general function without one or more limitations or inessential attributes), to the reference system.

As exemplified herein, at least one principal physical difference between two systems, apart from the computer control system, lies in differences between the first breathing circuit and the reference (second) breathing circuit. Implicitly, if the first breathing circuit and a reference breathing circuit (denoted for convenience as a "second" breathing circuit) are different, the respiratory gas delivery system of the invention, having regard to its operation within any reference respiratory gas delivery system, can be made compensatorily equivalent to the extent that the two systems are to intended to generally function equivalently. For example, features of the system of the invention and reference gas delivery system that may be made equivalent by simulating the features of the reference system may include a rate of flow from the gas delivery apparatus, cessation of flow e.g. to a patient airway interface (such as a breathing mask) to simulate cessation of flow upon expiration or a change of composition (e.g. volume triggered, for example, depletion of a volume of gas in a gas reservoir that is cyclically replenished, and depleted by inspiration) to simulate switching access between a gas reservoir and another flow path leading from an alternate gas source, optionally a reservoir or inlet, that may be used to introduce gas of a potentially different composition.

Accordingly, the present invention is also directed to a respiratory gas delivery system including, or adapted for use with, a first breathing circuit optionally having at least one gas conduit leading to a patient airway interface, characterized in that the respiratory gas delivery system virtualizes gas flow characteristics of a reference respiratory gas delivery system that includes a reference breathing circuit, the gas flow characteristics of the reference respiratory gas system dictated at least in part by structural features, for example components or parts, of the reference breathing circuit, the respiratory gas delivery system including:

a) a flow sensor, optionally positioned in or proximal to the patient airway interface; for determining, for example, the volume of gas entering the patient airway interface in a given breath or breath segment e.g. an inspiratory cycle or any portion thereof);

b) a gas delivery apparatus adapted to deliver a gas (the gas optionally comprising a plurality of component or constituent gases) into the patient airway interface, optionally into the gas conduit (the gas delivery apparatus may include an on-board computer for controlling the gas delivery apparatus and/or may adapted to receive input from an external computer); and optionally c) a gas analyzer, for determining, for example, the composition of gas exhaled by a subject, optionally at the end of exhalation, wherein the gas analyzer is optionally positioned in or proximal to the patient airway interface; and optionally d) a pressure transducer, optionally positioned in or proximal to the patient airway interface for determining, for example the beginning and end of each inspiratory cycle wherein the computer is programmed to control the gas delivery characteristics, particularly the gas output characteristics of the gas delivery apparatus such that the gas output characteristics of the gas delivery apparatus supplant structural features of the reference breathing circuit that dictate, at least in part, delivery characteristics of the reference respiratory gas delivery system.

The term "gas delivery characteristics" means any characteristic of a reference breathing circuit that affects gas flow to a subject that is dictated at least in part by a component of the circuit that is absent in the first breathing circuit. Optionally, the gas flow characteristic is dictated by one or more components or parts selected from a valve and a gas container such a reservoir, a conduit or compliance. Gas "delivery characteristics" or "flow characteristics" may include circuit pressure, the concentration of a gas constituent in a gas or in a component of a gas (for example as dictated by a change in the source or path of flow from a first circuit flow path to an alternate circuit flow path from which a gas of different composition emanates) a rate or volume of flow of a gas or gas component or constituent, flow generation or restriction (e.g. via a valve such as a one-way valve, a proportional control valve, a PID control valve or an on/off type) or release of a flow restriction (e.g. via a valve) including the chronology of same (for example, the order/timing of delivery of component gases, for example from alternative sources or flow paths, such as imposed by a passive valve (which may have a predetermined opening pressure) or active valve (e.g. a balloon valve), and the capacity, qualitative and optionally quantitative, to accumulate a gas such as in a compliance, conduit or reservoir. In one embodiment, as described below, the respiratory gas delivery system virtualizes the gas delivery characteristics of a reference delivery system employing a sequential gas delivery circuit, for example, of the type having an inspiratory gas reservoir (which may be replenished—e.g. filled at a selected rate), an expiratory gas reservoir or ambient air inlet, and a flow control system which allows gas to flow to the patient from the expiratory gas reservoir or ambient air inlet, only when the inspiratory reservoir is temporarily emptied (it may be refilled, for example by the gas delivery apparatus e.g. in the form of a gas blender before each next inspiratory cycle).

The term "reservoir" means a containment chamber, optionally of defined volume and may include a bag, tubing etc. The term "flow control system" or "air flow control system" means a system in which components or parts such as valve(s) and conduit(s) control the origin and/or destination of flow when alternative airflow pathways are exploitable.

The term "component" used in the context of the phrase structural component of a breathing circuit means any portion of a breathing circuit and includes an assembly of interacting parts designed to perform a function, for example an inspiratory limb of a breathing circuit, an expiratory limb of a breathing circuit, a reservoir with an inlet and outlet portion etc. The term part is used interchangeably with the proviso that the term part in this connection denotes any part, but in contrast to component is not intended to denote an assembly of parts if any part is of the type that would typically be produced or sold as an indivisible unit i.e. a part is exemplified by a part of a valve or a valve typically produced or sold as a unit but not a valve connected between to independent air conduits.

The term "computer" is used broadly to refer to any device (constituted by one or any suitable combination of components) which may be used in conjunction with discrete electronic components and/or parts e.g. valves to perform the functions contemplated herein, including computing and obtaining input signals and providing output signals, and optionally storing data for computation, for example inputs/outputs to and from electronic components and application specific device components as contemplated herein. As contemplated herein a signal processor or processing device in the form of a computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from—a pressure transducer, a gas analyzer, any type of input device for inputting parameters or values (for example, a knob, dial, keyboard, keypad, mouse, touch screen etc.), input from a computer readable memory etc. Key outputs may include output to a flow controller (e.g. PI control or PID control etc.). The term "processor" and "computer" are used interchangeably.

Excluded from the invention are respiratory gas delivery system used to monitor pressure in a system to control active valves leading to two physical reservoirs containing gases of differing compositions. The system of the invention obviates reliance on two circuit flow path leading to two gas reservoirs, and the related requirement to coordinate flow between the paths, for example, if desired to avoid any interruption in flow or conjoining of different sources of gas flow.

The term "virtualizes" refers to programmed gas delivery in accordance with a model of a practical or "theoretical" circuit, the virtual circuit of the model replacing or obviating completely ("supplanting") structural features of a reference gas delivery system, particularly at least one component of a reference breathing circuit, which the reference delivery system is adapted to operate with. The structural component(s) is thereby supplanted by delivery apparatus output characteristics.

The term "sequential gas delivery (SGD for short) valve" means any valve that enables two gases to be delivered in sequence when a physical or virtual criterion is met. For example, the criterion may be depletion of a reservoir set to contain a limited amount (e.g. expressed as volume) of a gas so that at least one other gas is delivered in the same breath. Such a physical valve may be an active valve (e.g. a balloon valve) or a passive valve with an elevated opening pressure which provides for gas flow e.g. in the context of a rebreathing circuit, responsive only to depletion of a first gas source which is accessible at a lower pressure e.g. via a valve with a lower opening pressure (see FIGS. 2 and 3 and WO/2004/073779 which discloses examples of such valves and related circuits).

According to one embodiment, a theoretical circuit is exemplified by a circuit can be idealized to function free of a particular limitation that is hard to realize to a near ideal extent in practice, but for the invention which simulates the circuit functioning close to ideally (e.g. in at least one manner selected from less complex, less bulky, less prone to failure, capable of instantaneous changes in composition to simulate switching between different gas sources e.g. where cessation of flow from one source and commencement of flow from another source is hard to synchronize when the sources are switched physically as opposed to virtually e.g. by modeling the sources and the criteria for switching e.g. temporary depletion of a source which is alternately replenished and depleted at a selectable or ascertainable rate, triggering flow from an alternate source when depleted (in virtual terms—a change in composition upon depletion where the criterion for specifying the composition, if variable, from that alternate source, so dictates). Such a virtual circuit can be seen to do away with the switching apparatus of a breathing circuit (optionally including the physical source itself e.g. a gas reservoir, as well as associated gas conduits and valves e.g. an SGD valve) and the need for multiple physical sources of the breathing circuit. Modeling of the sources can be accomplished in terms of at least one parameter selected from composition and pattern of flow including at least one of rate of flow, volume of flow, duration of flow, flow pressure.

Optionally, the gas delivery characteristics of the reference breathing circuit are dictated in part by an inspiratory limb of the circuit including an inspiratory gas reservoir. The inspiratory gas reservoir may be supplanted in the first breathing circuit by control of the gas delivery apparatus so as to simulate replenishment e.g. filling (simulated by flow to the patient of a component gas of first composition) and depletion (for example, as measured by a flow sensor positioned to measure the actual inspiratory flow rate of a subject) of the inspiratory gas reservoir (arrest of flow of the component gas of first composition). The term "inspiratory gas reservoir" is used to refer to a reservoir for a gas composition that provides the first part of the gas content of each breath, for example: (1) the patient's primary respiratory requirements or (2) a gas that is primarily intended to create a concentration gradient to promote gas exchange with the pulmonary circulation. By contrast, the goal of delivering an exhaled gas or gas of similar composition (a neutral gas) is on the contrary (intended to avoid creating such a concentration gradient) except, optionally, in so far as its delivery is also secondarily intended to conserve a gas e.g. oxygen, an anesthetic or other therapeutic/diagnostic gas.

The term "delivery" or "deliver" is used to refer to making a gas available to a subject for inspiration and does not imply that a pressurized source is opened to a subject. For example, a gas may be made available from a reservoir or conduit (passively) when no resistance exists to its inhalation or such resistance is able to be overcome by an inspiratory effort of a subject with or without mechanical assistance.

Optionally the flow characteristics of the reference breathing circuit are dictated in part by a flow control system which directs gas flow from a first source or circuit flow path for a first gas component, for example an inspiratory reservoir of the reference breathing circuit, to an alternate source or circuit flow path for a second gas component, for example, an air intake port or a second gas reservoir (for example an expiratory gas reservoir) when structural features of the reference breathing circuit arrest flow from the first gas source, for example when the volume of the inspiratory reservoir is depleted or when a valve is set to restrict flow from the first gas source. The flow control system is optionally supplanted in the first breathing circuit by programed gas output characteristics which first match those of the first gas source or circuit flow path, and subsequently, corresponding to when flow switches to the alternate gas source or circuit flow path, match those of the alternate gas source or circuit flow path. For example, the gas flow characteristics may include concentration and/or volume of at least one constituent of gas emanating from the first gas source or circuit flow path (a constituent of the first gas component) and the concentration of at least one constituent gas of the gas emanating from the second gas source or circuit flow path (a constituent of the second gas component).

According to one aspect, the present invention is directed to a respiratory gas delivery system including or adapted for use with a first breathing circuit optionally comprising or consisting of at least one gas conduit leading to a patient airway interface, characterized in that the respiratory gas delivery system is adapted to virtualize, for example, simulate the function, for example selected gas flow (delivery) characteristics, of a reference respiratory gas delivery system which includes or is adapted for use with a second, reference breathing circuit, that is structurally different (e.g. less wasteful of gas and/or less complex (e.g. fewer parts or parts more easy to assemble, integrate or coordinate) and/or less bulky, and/or less expensive and/or less prone to failure or physical limitations), the respiratory gas delivery system including:
- a) a flow sensor, optionally positioned in or proximal to the patient airway interface;
- b) a gas delivery apparatus adapted to delver a gas comprising a plurality of component or constituent gases into the patient airway interface, optionally into the gas conduit (the gas delivery apparatus may include an onboard computer for controlling the gas delivery apparatus and/or may adapted to receive input from an external computer); and optionally
- c) a gas analyzer, wherein the gas analyzer is optionally positioned in or proximal to the patient airway interface;

wherein control of the gas delivery apparatus simulates selected flow characteristics of the reference gas respiratory gas delivery system that:
1. are defined at least in part by structural features, for example, structural parts of the reference breathing circuit,
2. define the source or circuit flow path and/or order of delivery of one or more component gases, and/or the composition and volume of the gas or a component or constituent of the gas made available for inspiration in a breath, series of breaths, breath segment or series of breath segments, or time period;

and wherein the computer is programed provide inputs to the gas delivery apparatus to:
- A) control the gas delivery apparatus by executing an algorithm that employs as inputs data obtained from the flow sensor (and optionally the gas analyzer) and at least a mathematical model of the second, reference breathing circuit, including parameters that describe supplanted structural features e.g. structural parts of the second, reference breathing circuit, the supplanted features e.g. structural parts:
  - a. defining at least in part the selected gas delivery characteristics;
  - b. absent in the first breathing circuit; and
- B) generate an output signal to the gas delivery apparatus that accounts for the supplanted structural features of the second, reference breathing circuit, such that when the respiratory gas delivery system outputs gas to the first breathing circuit the selected gas output characteristics of the respiratory gas delivery system simulate portions of the reference respiratory gas delivery system defined by the supplanted parts of the second reference breathing circuit.

In one embodiment, the reference breathing circuit is a rebreathing circuit including an inspiratory gas reservoir that is absent in the first breathing circuit, the computer programmed to obtain input of at least one rate at which the inspiratory gas reservoir is filled and at least one rate at which the inspiratory gas reservoir is emptied and to control the gas delivery apparatus to deliver a carbon dioxide containing gas after simulated depletion of the inspiratory gas reservoir.

In one embodiment, the reference breathing circuit is a rebreathing circuit including an inspiratory gas reservoir and an expiratory gas reservoir that are absent in the first breathing circuit, the computer supplanting the inspiratory and expiratory gas reservoirs, optionally by obtaining input of at least one rate at which the inspiratory gas reservoir is filled (this is optional since a first gas reservoir of a selected volume can simply be assumed to be replenished at beginning of each inspiratory cycle) and at least one rate at which the inspiratory gas reservoir is emptied, and controlling the gas delivery apparatus to deliver a carbon dioxide containing gas after each simulated depletion of the inspiratory gas reservoir. A rebreathing circuit may be a sequential gas delivery circuit if component gases are delivered in sequence. A sequential gas delivery circuit does not imply that the gas delivered after the first gas composition is or has the composition of at least one component e.g. $CO_2$ of an exhaled gas in an amount corresponding to a last exhaled end tidal gas, or a target concentration of an end tidal gas if the respiratory gas delivery system is adapted to control same.

In one embodiment, the respiratory gas delivery system includes a gas analyzer and the reference breathing circuit is a sequential gas delivery circuit. The first delivered gas may be of a composition that primarily corresponds to the patient's physiological and/or therapeutic gas requirements while the second delivered gas may be exhaled gas or a gas formulated by the gas delivery apparatus e.g. a gas blender containing at least those constituents of the exhaled gas in amounts that justify its delivery e.g. delivery of carbon dioxide in amount that represents its intended function as a "neutral gas" as defined below.

In one embodiment, the respiratory gas delivery system includes a gas analyzer, and the reference breathing circuit comprises an inspiratory gas reservoir, an expiratory gas reservoir and air flow control system for directing the flow of gas to the patient only when the inspiratory gas reservoir is depleted. The airflow control system may typically include one or more active and/or passive valves (activated when a threshold pressure is reached, e.g. negative pressure resulting from depletion of the inspiratory gas reservoir). The reference breathing circuit may include a flow control system including a by-pass limb interconnecting an inspiratory and expiratory limb of the circuit or a by-pass limb located exclusively within an expiratory limb of the circuit and therefore functioning to utilize negative inspiratory pressure to draw on the expiratory gas flow path when gas sourced from inspiratory flow path is depleted. Alternatively, one or more active valves can be used to effect sequential gas delivery (see US Patent Publication No. 2007/0062534). The inspiratory reservoir, expiratory gas reservoir and/or flow control system may absent from the first breathing circuit. The gas delivery apparatus may be programmed to control the concentration and rate of flow of the gas to simulate one or more cycles of filling and depletion of the inspiratory gas reservoir, optionally based on at least one rate of flow of gas into the inspiratory gas reservoir and at least one rate at which the inspiratory gas reservoir is depleted, and where input of at least one constituent of the gas exhaled by the subject is obtained from the gas analyzer for setting the gas delivery apparatus to (e.g. subsequently or contemporaneously) deliver a gas containing the at least one constituent in a selected concentration, for example a concentration that matches or approximates the concentration measured by the gas analyzer (optionally carbon dioxide).

With reference to any aspect of the present invention, in one embodiment, the second, reference breathing circuit is a rebreathing circuit, and the gas delivery apparatus optionally simulates filling of an inspiratory gas reservoir at a rate of flow that is less that the subject's minute ventilation minus anatomic dead space ventilation. In this manner, the entirety of a first delivered gas of selected composition makes its way into the alveolar volume of the lung (as opposed to the anatomic dead space). A gas that has a composition that corresponds to that of subject's exhaled gas from a breath n−1 may then be delivered in each breath n, for example, upon simulated depletion of the inspiratory gas reservoir. In a broader sense, the second delivered gas may a "neutral gas" (defined below), for example, in the sense that its composition, in terms of at least one of its constituents e.g. carbon dioxide, contributes minimally to establishing a partial pressure gradient between the lung and pulmonary circulation. In one embodiment, the selected gas output characteristics comprise at least one of the following:

(i) the order or timing of delivery of two components of the gas, for example, wherein delivery of one component of the gas is first, followed by, a second component of the gas, optionally, delivery of the first component ceasing pending delivery of second component of the gas and vice versa, in cycles. Preferably the respiratory gas delivery system simulates a reference respiratory gas delivery system in which the rate of flow of the first component is less than the subject's minute ventilation minus anatomic dead space ventilation such the entire volume of the first delivered component enters the alveolar space, in each cycle, the second component being a neutral gas;

(ii) the volume and composition per breath or breath segment of the gas or at least one constituent of the gas;

(iii) the volume of a component or constituent of the gas relative to a total delivered volume of the gas, over a plurality of breaths or breath segments or over any time period [t];

(iv) a concentration of at least one component or constituent of the gas in each incremental unit of volume of the gas output from the gas delivery apparatus;

(v) a subject's effective alveolar ventilation in a breath [i] or over a plurality of breaths [n] or over a selected time period [t]. The term "effective alveolar ventilation" means the part of the volume of delivered gas that reaches the alveoli and establishes a concentration gradient for gas exchange (excludes the "neutral gas" component).

According to one aspect, the invention is directed to a respiratory gas delivery system adapted for use with a first breathing circuit having at least one gas conduit leading to a patient airway interface, characterized in that the respiratory gas delivery system virtualizes structural components a reference breathing circuit, the respiratory gas delivery system including:

a) a flow sensor, positioned for at least determining the volume gas inhaled via the patient airway interface;

b) a gas delivery apparatus including or controlled by a computer for delivering a gas comprising a plurality of component or constituent gases into the patient airway interface; and optionally c) a gas analyzer for analyzing the gas concentration of one or more constituent gases inhaled and/or exhaled by the subject;

wherein the computer is programmed to supplant one or more components of the reference breathing circuit by using a mathematical model of the supplanted structural components to generate gas delivery characteristics that supplant said components.

As suggested, the term supplants includes making one or more components superfluous (unnecessary to have a physical counterpart in the first breathing circuit) or replacing it/them with another/other component(s), for example, such that the supplanted circuit needs fewer, and/or less bulky and/or less complex or costly and/or components less prone to failure.

Optionally, the respiratory gas delivery system comprises virtual components which simulate components of a reference breathing system.

For example, in one embodiment, the supplanted component is an inspiratory gas reservoir which may be superfluous in the first breathing circuit. For example, the respiratory gas delivery system may be programmed to deliver a gas which, in effect, repeatedly (cyclically) provides the composition of the inspiratory gas reservoir in volumes which match the virtual content of inspiratory gas reservoir as it filled and re-filled virtually having regard to the timing rate of flow in and out of the virtual reservoir, so that a counterpart physical reservoir is obviated in the first breathing circuit and accordingly in the design of the respiratory gas delivery system as a whole.

For example, in one embodiment, the supplanted component is a sequential gas delivery valve or valve set which may be superfluous in the first breathing circuit. A sequential gas delivery valve or valve set means a valve or valve set that alternately directs flow from a first flow path to a second flow path, for example so that differently constituted and/or sourced gases may be delivered, for example a first gas that supplies some part of the content requirements of the gas inspired in a given inspiratory cycle and a second gas that supplies the other part of that content (for example a "neutral" gas e.g. an end tidal gas. For example, the respiratory gas delivery system may be programmed to first deliver a gas which, in effect, repeatedly (cyclically) provides the composition of an inspiratory gas reservoir, and then ambient air inlet or the putative content of a virtual second gas reservoir. Accordingly, in terms of physical components of the first breathing circuit a single conduit leading to the patient airway interface may replace the aforementioned valves and optionally a second gas reservoir e.g. an expiratory gas reservoir.

DETAILED DESCRIPTION OF PREFERRED EMBODIMENT

Figure 1:
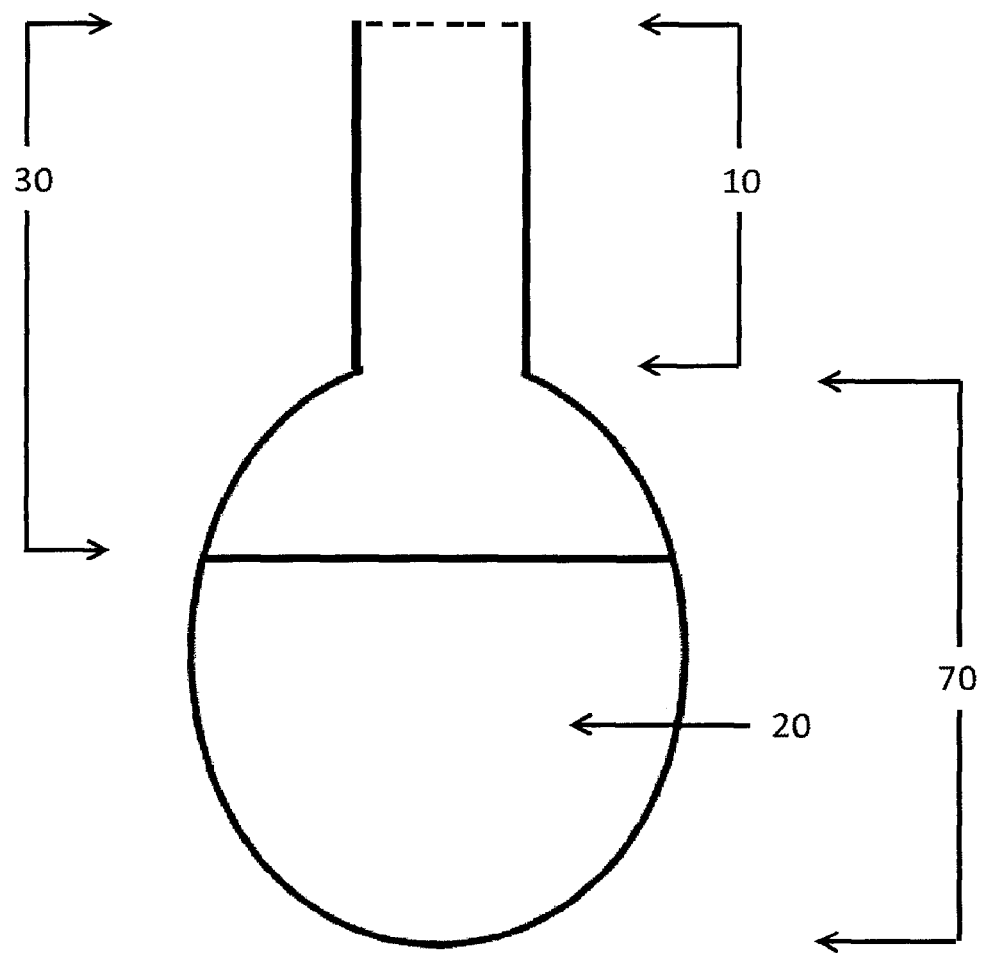
FIG. 1 is a schematic representation of a lung illustrating how sequentially delivered components of a respiratory gas may contribute differentially to gas exchange with the pulmonary circulation.

The term "component" used with reference to delivery of a portion of a gas refers to a distinct functional subset of the gas that may, if desired, be delivered separately by the respiratory gas delivered system (and conventionally is delivered separately in the reference respiratory gas delivery system), for example over a different time frame e.g. in sequence with another component as in a sequential gas delivery (SGD) circuit, whereas a "constituent" of the gas is considered by definition already part of a blend of gases of different chemical composition (even in the reference system) that can no longer be delivered separately unless first separated. Typically, constituents include individual or blended gases stored in a tanks for use in conjunction with a gas delivery apparatus in the form a gas blender for example as disclosed, in WO/2007/012197, for example to target an end tidal concentration of a gas X which is present alone or in a blend of gases from a particular tank or source (preferably stored or deliverable under pressure). An end tidal concentration of gas X may be controlled by methods well known to those skilled in the art including the method disclosed in WO/2007/012197 and Slessarev M. et al., J Physiol 581.3 (2007) p. 1207. A constituent gas is therefore considered indivisible without forced separation of its component parts. For example, to deriver a gas composition that targets a partial pressure of carbon dioxide of 50 mm. Hg a gas composition that empirically causes an increase in the partial pressure of CO2 to the desired partial pressure e.g. 8% $CO_2$ and the algorithm disclosed in WO/2007/012197 can be used to maintain this partial pressure.

The term "mathematical model" is used broadly to refer to any model in which any form of a mathematical relationship or computation underlies or is involved in a process executed by a computer and for greater certainty includes a model embodied in a look up table.

The term "algorithm" or related terms such as "algorithmic" (e.g. algorithmic model") refers to any processor set of rules to be followed by a computer in performing a function of the computer, in particular, simulation of one or more components of a reference breathing circuit.

As used herein, in the context of simulating structural features of a reference breathing circuit, and in particular, a sequential gas delivery circuit, simulation could not be carried without at least one if not both of a "mathematical model" and an "algorithmic model" and each may be understood to encompass the other.

As used herein the term "specifiable" implies that a convenient input means is available to a user to specify a parameter or value whereas the term "specified" implies that some parameter or value is set, regardless of whether it is pre-set or obtained by such convenient input. Hence unless used in the phrase "specifiable or specified" the term "specified" does not imply that a value or parameter was not specifiable. The phrase "specifiable or specified" is used herein for convenience to imply that the facility for user input either is or is not readily available without commenting on whether a facility to make a parameter or value "specifiable" is necessary. The convenience of having the facility of a specifiable input can generally be understood to be optional and generally preferred (for potential non-immediate or anticipated or unanticipated future uses, or testing) regardless of whether this facility is needed for using the invention to the most advantageous or most practical extent of its capability, redundant or of no foreseen value provided that the invention can be used only for very narrow purposes or to only modest advantage without this facility.

The term "gas delivery apparatus" is any apparatus that is capable of modulating the composition of an inspiratory gas, for example any device that can make a gas of variable/selectable composition available for inspiration. The gas delivery apparatus may be used in conjunction with a ventilator or any other respiratory assistance device associated with a breathing circuit from which the subject is able to inspire a gas of variable/controllable composition.

Preferably, the composition of the gas and/or flow rate is under computer control. For example, a gas delivery apparatus may be adapted to deliver at least one gas (pure or pre-blended) at a suitable pre-defined rate of flow. The rate of flow may be selectable using a form of input device such a dial, lever, mouse, key board, touch pad or touch screen. Preferably the gas delivery apparatus provides for one or more pure or blended gases to be combined i.e. "a gas blender".

A "gas blender" means a device that combines one or more stored (optionally stored under pressure or delivered by a pump) gases in a pre-defined or selectable proportion for delivery a selectable rate of flow, preferably under computer control. For example one or more stored gases may be combined with pumped room air or a combination of pure or blended (each blended gas may have at least 10% oxygen for safety) gases respectively contain one of carbon dioxide, oxygen and nitrogen as the sole or predominant component. Optionally, the selectable proportion is controlled automatically using an input device, optionally by variably controlling the flow of each stored gas (pure or pre-blended) separately, preferably using rapid flow controllers, to enable various concentrations or partial pressures of a gas X to be selected at will within a pre-defined narrow or broad range. For example, the gas blender may be a high flow blender which blows gas past the mouth (i.e. in which gas that is not inspired is vented to the room) or the gas blender may be adapted to conserve gas by delivering gas in volumes that closely match the patient's volume requirements of a breath.

Optionally, the respiratory gas delivery apparatus contain the basic structural or specialized algorithmic features described in WO/2012/139204.

The term "reached" when used to describe reaching a threshold volume means attained or exceeded.

The term "criterion" means any state or condition for which input needed to determine whether or not the condition is satisfied or the state is present is usable by a processor operatively associated with a respiratory gas delivery system of the invention, optionally input from a measurement device of any kind (e.g. pressure, flow, concentration) that is operatively associated with the respiratory gas delivery system, optionally a measurement device operatively associated a breathing circuit within or proximal to a patient airway interface.

A "rebreathing circuit" or "partial rebreathing circuit" is any breathing circuit in which a subject's gas requirements for an inspiratory cycle are made up in part by a first gas of a selectable composition and a rebreathed gas to the extent that the first gas does not fully satisfy the subject's volume gas requirements for the breath. The first gas must be selectable in at least one of composition or amount. Preferably the amount and composition of the first gas is selectable. The rebreathed gas composition optionally consists of previously exhaled gas that has been stored or a gas formulated to have the same concentration of gas X as previously exhaled gas or a second gas has a gas X concentration that is selected to correspond (i.e. has the same concentration) to that of the targeted end tidal gas composition for a respective breath [i]. Aspects of invention related to the sequential delivery of such components may not apply where the subject's requirements for a breath are over-estimated or where it otherwise not necessary that the entirety of the first gas component make it the alveolar portion of the lung.

Preferably the circuit is designed or employable so that the subject receives the entirety of or a known amount of the first gas in every breath or in a consecutive series of breaths forming part of gas delivery regimen. In a general sense a re-breathed gas serves a key role in that it does not contribute significantly to the partial pressure gradient for gas flow between the lung and the pulmonary circulation when intake of the gas at least fills the entirety of the anatomic dead space. Therefore, in the case of a spontaneously breathing subject (whose tidal volume is not controlled e.g. via a ventilator) the subject's unpredictable tidal volume does not defeat prospective computation of the controlled gas composition required to attain or target an end tidal partial pressure of a gas x (PetX[i]) for a respective breath [i].

Optionally, the "rebreathed gas" may be constituted by or substituted by a prepared gas (in terms of its gas X content). Thus, according to one embodiment of the invention, the second gas has a gas X concentration that is selected to correspond to that of the targeted end tidal gas composition for a respective breath [i]. The volume of the first inspired gas may also be adjusted (e.g. reduced) to target PetX[i]T for a respective breath [i] such that the subject receives an optimal amount of a gas having a gas X concentration that corresponds to a target PetX[i]T. Target end tidal concentrations of gas x may be achieved with a device called a Respiract™ (see WO/2007/012197).

As alluded to above, it will be appreciated that the gas X content of a prepared gas can be formulated to represent a gas of a "neutral" composition. Thus the total inspired gas for a respective breath [i] will comprise a first inspired gas having a controlled volume and gas X concentration (FIX) and a second gas which has a gas X content whose contribution to establishing a partial pressure gradient between the lung and pulmonary circulation is optionally minimized. In a broader sense, the second inspired gas content of gas X can be optimized to attain a targeted end tidal concentration (for a universal set of circumstances) and in a sub-optimal sense this concentration at least does not defeat the ability to prospectively compute an FIX for the purposes of attaining or targeting a PetX[i] for a respective breath [i] (i.e. not knowing the subject's tidal volume for a respective breath [i] will not preclude such computation).

The term "sequential gas delivery circuit" means a breathing circuit in which a first gas, optionally of selectable first composition (e.g. using a gas blender) is delivered first, and a second gas of second composition is delivered later than, optionally after delivery of the first gas, optionally when the first gas is depleted. A sequential gas delivery circuit optionally comprises first and second gas reservoirs and optionally a flow control system (e.g. a valve or series of valves and conduits) for switching repeatedly, optionally in each inspiration cycle, between a first circuit flow path in which the first gas reservoir is drawn upon and a second circuit flow path in which the second gas reservoir is drawn upon. Optionally, the trigger for switching between first and second flow paths is circuit pressure, for example the trigger is generated by an increase in circuit negative pressure when the first gas reservoir is depleted (opening a passive valve leading to second circuit flow path) or for example, a pressure transducer serves as input to alternatively open and close the first and second flow paths. The elapse of time, a gas analyzer reading etc. may also be a trigger.

As seen in FIG. 1, the gas entering the lung may be schematically divided into the alveolar portion 70 which contributes to gas exchange with the pulmonary circulation and the anatomical dead space portion 10, which includes the trachea, bronchi, and bronchioles, namely portions of the lung which carry gas to and from the alveoli, but do not directly contribute to gas exchange. According to one example of a reference breathing circuit, a sequential gas delivery circuit, best seen in FIG. 3, by setting the rate of flow of gas into an inspiratory reservoir to be less than the minute ventilation, optionally less than the minute ventilation minus anatomical dead space ventilation. Gas sourced from a freshly filled inspiratory gas reservoir, when delivered first, occupies a portion of alveolar space 20 which therefore defines the effective alveolar ventilation, since the remainder of the gas making up the subject's inspiratory requirements 30 may be a second delivered gas which is an end tidal gas or a gas of the same approximate composition, which is "neutral" from the standpoint of gas exchange (i.e. it is already equilibrated with the partial pressure of those gases in the pulmonary circulation).

Accordingly, during any inspiration, the gas that is inspired first reaches the alveoli, while the gas inspired towards the end of the inspiratory cycle remains in the anatomical dead space. Many gases administered in clinical or research situations must enter the blood through the alveoli to exert the intended physiological effect. Inhalational anaesthetics such as nitrous oxide or isoflurane are a common example. The portion of such a gas that remains in the anatomical dead space does not enter the blood and do not produce any physiological effect. This portion of the gas is therefore wasted. It would be advantageous to deliver these gases only during the first part of inspiration that enters the alveoli.

This invention can accomplish this by signalling the gas delivery device to provide the gas of interest for a first defined volume of every inspiration, and then turning off delivery of the gas of interest only (setting its concentration in the inspired gas mixture to zero) in any volume inspired beyond the first volume.

Figure 2:
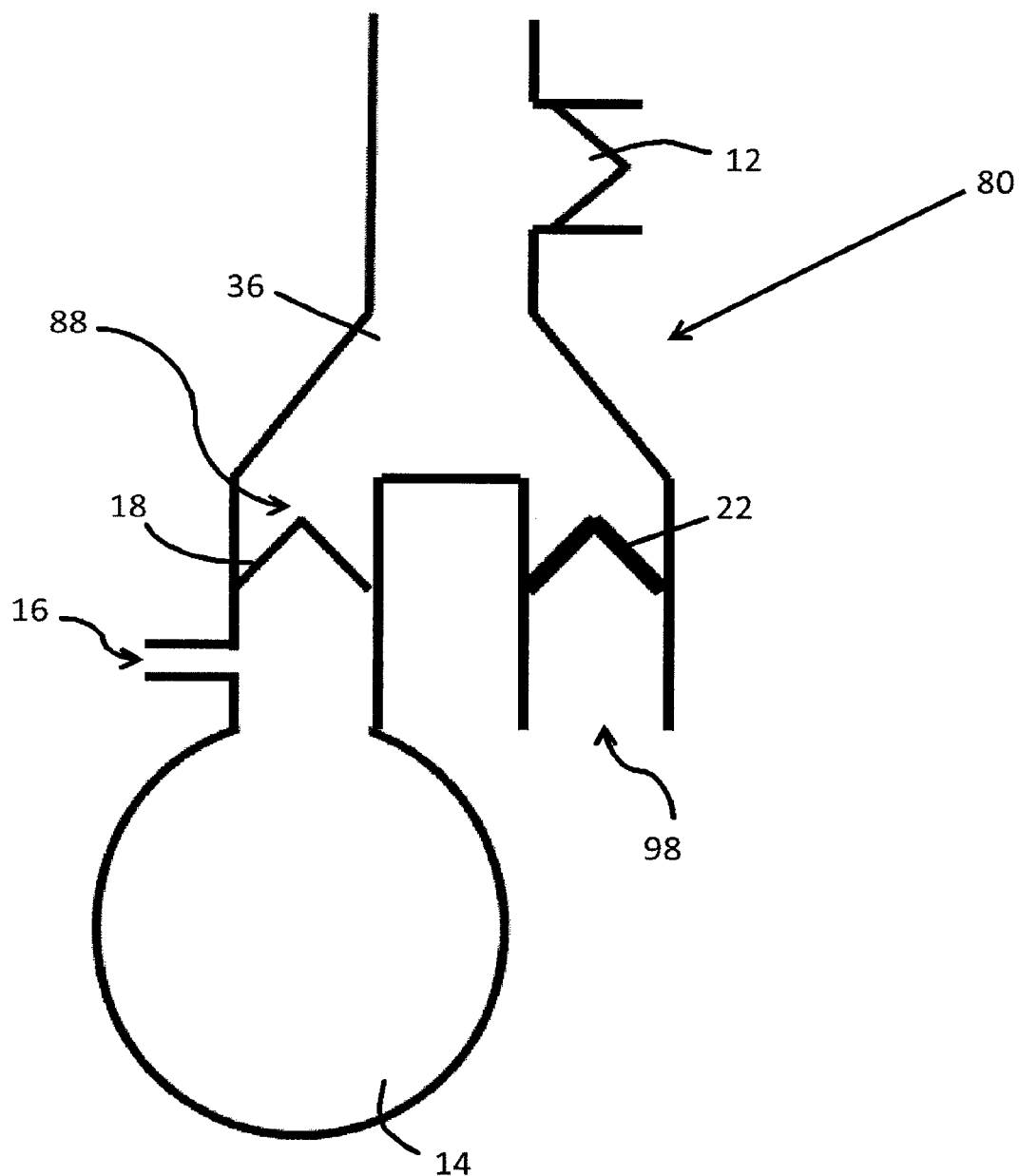
FIG. 2 is a schematic representation of one example of a reference breathing circuit.
Figure 3:
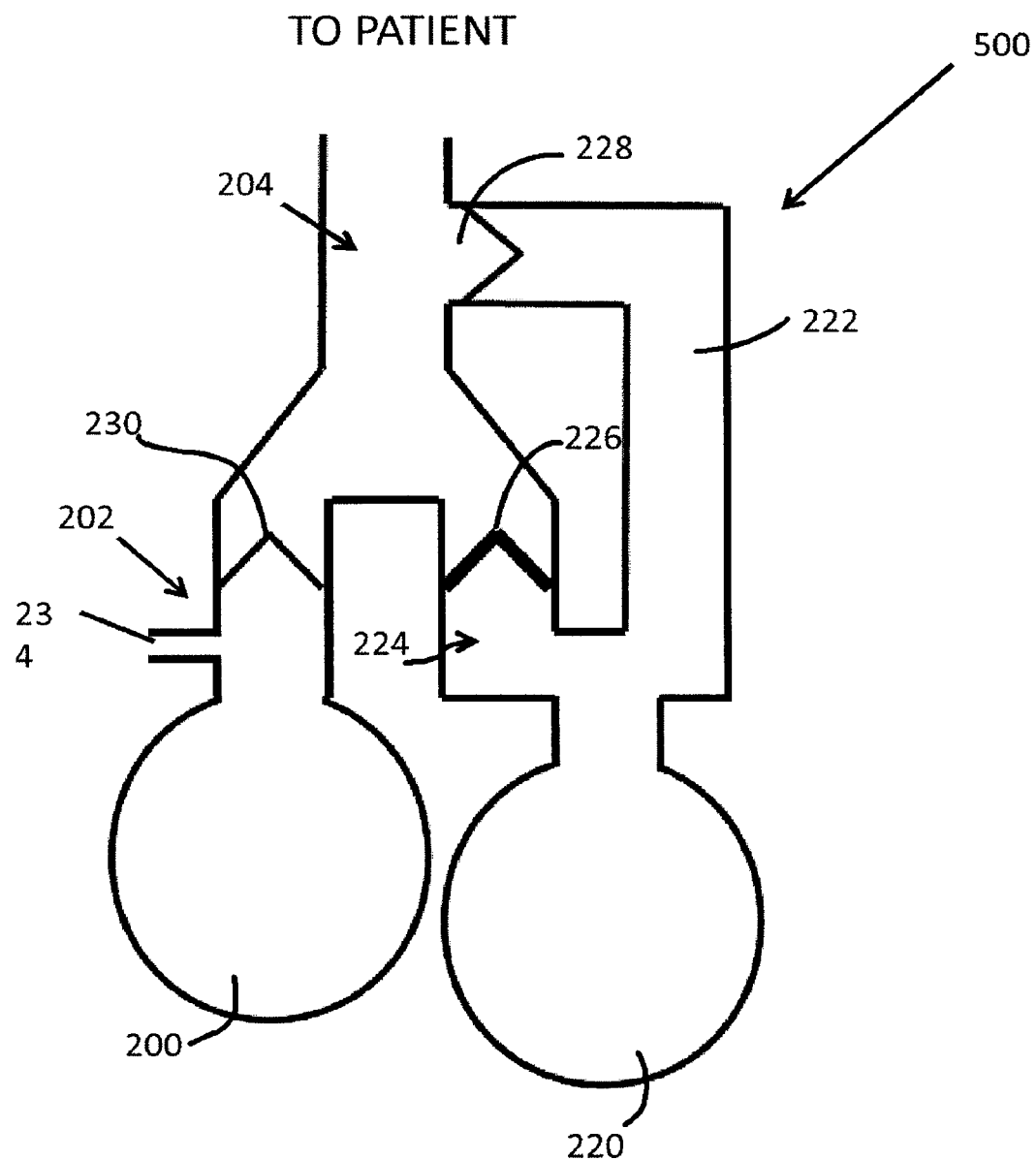
FIG. 3 is a schematic representation of another example of a reference breathing circuit.

In one aspect the invention, is directed to a gas delivery apparatus programmed to modulate the composition of the inspiratory gas throughout the inspiratory phase of the breath. The composition of the inspiratory gas may optionally be changed according to the cumulative volume of gas inspired. The invention may be used to provide inspiratory gases to a subject, which are equivalent to those that would have been inspired through a particular physical breathing circuit, for example as illustrated in FIGS. 2 and 3. Alternatively, the invention simulates a breathing circuit for which there is no practical physical embodiment. It will be appreciated that certain features of a reference breathing circuit that would be impractical to construct owing to technical challenges (for example, an SGD manifold that is small enough not to be obstructive, flexible gas tubing which does not expand under pressure etc.) may be able to be sufficiently "simulated" by the respiratory gas delivery system of the invention to obviate or minimize such technical challenges. Hence, the terms "respiratory gas delivery system" and "first breathing circuit" encompass virtual systems and circuits which are limited only by the physical limitations of any necessary components selected from at least one of flow sensors, gas analyzers, gas delivery devices (e.g. valves) and flow controllers (e.g. response time, volumetric capability, sensitivity and precision) associated with implementing gas blending and delivery into a simple conduit connected to a patient airway interface.

Similarly the term "simulated" broadly refers to any algorithm which models a practical or "only theoretically" feasible system/circuit, which system/circuit is susceptible of algorithmic modeling, graphical representation and/or mathematical definition to implement a physical system which uses the simulation algorithm as input. For greater certainty, it is to be understood that while at least one component of the reference system of interest (including at least one component of the reference breathing circuit) is being simulated, inputs to the simulation algorithm (e.g. inspiratory flow) may be obtained from a real (i.e. not simulated) system (e.g. a flow sensor connected to a real patient) and the outputs from the simulation algorithm directed to a real (i.e. not simulated) system (e.g. a gas delivery apparatus which may then deliver gas to a real subject). Accordingly, the at least one component of the breathing is circuit may "simulated" in order to replace at least one component of an otherwise embodied ("real") system usable for therapeutic and/or diagnostic or experimental gas delivery, not to be confused with an in silico system that resides solely on a computer for teaching, training or other modelling purposes. In the result, a breathing circuit may be "simulated" at least in part in order to provide the same physical function as that provided by, or postulated for, a reference circuit, for example, using a mathematical function (equation) or a look-up table such that real physical measurements may be obtained and used to calculate and then control a matching output of gas from a gas controller.

The term "matches" and related terms and "tracks" and related terms (implying an equivalent amount or rate) Imply a substantial identity which is substantially functionally equivalent qualitatively and quantitatively (subject to only optional correction or avoidance of inferior or inconsequential features).

The subject breathes from gas delivered by a gas delivery apparatus. According to one embodiment, the invention contemplates that a flow sensor is positioned proximal to the subject's airway to measure the flow of inspired gas. The apparatus also comprises a computer in the form of a microprocessor or other computing means. The microprocessor reads the output of the flow sensor. The flow signal may be integrated to compute inspired volume. The microprocessor signals the gas delivery apparatus to deliver specific compositions of inspired gas based on the cumulative inspired volume.

For example, according to one embodiment, illustrated in FIG. 2, the function of the reference Hi-Ox 80 circuit may be approximated by this respiratory gas delivery system according to the present invention. As seen in FIG. 2, one example of a reference breathing circuit is a sequential gas delivery circuit 80 including an inspiratory limb of the circuit 88 comprising a first gas inlet 16 that fills a gas reservoir 14 in the form of an inspiratory gas reservoir. A one-way inspiratory valve 18 enables, for example, a spontaneously breathing subject, to draw on gas in the inspiratory gas reservoir 14 so that gas enters a bifurcated portion of the circuit 36 (optionally a y-piece) to the patient. The patient exhales through one-way expiratory valve 12. When the inspiratory gas reservoir 14 is depleted, valve 22, which opens at a higher pressure than one-way valve 18, responds to the increase in negative pressure, enabling a subject to draw fresh air from the ambient air port 98 for the remainder of that inspiration.

Figure 4:
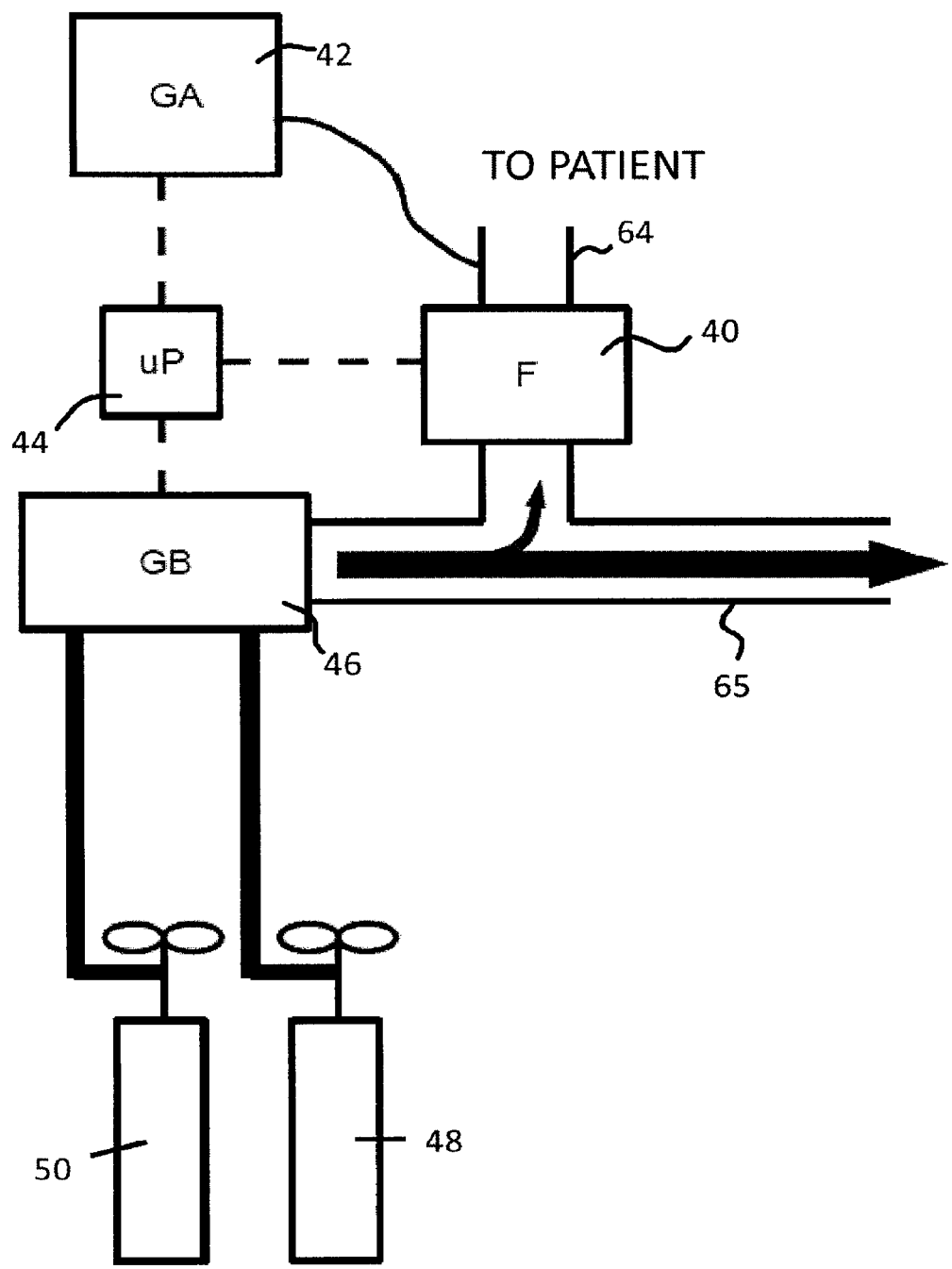
FIG. 4 is a schematic representation of one embodiment of a respiratory gas delivery system according to the invention.

As seen in FIG. 4, according to one embodiment of a respiratory gas delivery system according to the invention, a reference breathing circuit is virtualized using a gas blender 46 to control gas delivery characteristics (at least one of flow rate and composition) of the gas flowing through conduit 65. Gas inspired by the patient is drawn from the stream flowing though conduit 65 via conduit 64. The flow rate though conduit 65 is greater than the maximum inspiratory flow of the patient. The flow sensor 40 associated with conduit 64 determines the volume of gas inspired by the patient. One or more gas analyzers 42 may be used to analyze gas in conduit 64. For example gas exhaled by the patient may be analyzed in conduit 64, for example, depending on the gas of interest, via an NO2 analyzer and/or a CO2 analyzer. Gas blender 46 blends gas from two pressurized sources 50 and 48 and is controlled by microprocessor 44 which receives input from the gas analyzer 42 and flow sensor 40. The microprocessor signals the gas delivery apparatus to provide oxygen for a first predefined volume of any inspiration, and air for any volume inspired beyond the first volume.

This is an only approximation of the Hi-Ox 80 since the volume of high oxygen gas inspired during the first part of the inspiratory cycle is fixed, while with the Hi-Ox 80 it is dependent on the volume accumulated in the reservoir.

Alternatively, the function of the Hi-Ox 80 may be more exactly simulated by the device by accounting for the filling of the reservoir. Here, the microprocessor can be programmed to calculate the volume of oxygen that would be in the reservoir of a Hi-Ox 80, and switch the composition of the inspired gas to air when the calculated volume in the virtual reservoir is zero. In this embodiment, the operator programs the microprocessor with a virtual rate at which the virtual reservoir is to fill. The microprocessor continually increases the volume in the virtual reservoir at the specified virtual flow rate throughout the entire breath. For the first part of any inspiration, the microprocessor signals the gas delivery device to deliver oxygen to the subject. While the subject inspires oxygen, the volume in the virtual reservoir is decreased at the inspiratory flow rate measured by the flow sensor. When the virtual reservoir is empty, the microprocessor signals the gas delivery device to deliver air for the remainder of the current inspiration. While the subject inspires air, the volume of the virtual reservoir is not decreased at the inspiratory flow rate. In this way, the invention allows a subject to inspire the exact same gases as with a physical Hi-Ox 80 circuit with an oxygen reservoir that is being filled at a constant flow rate.

Figure 5:
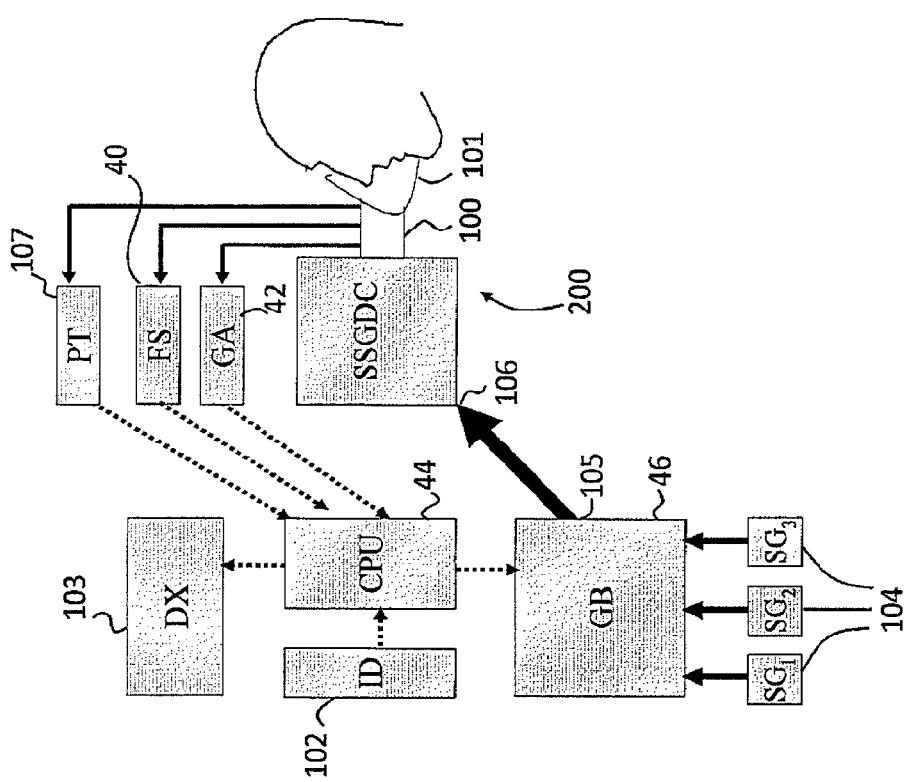
FIG. 5 is a schematic representation of another embodiment of a respiratory gas delivery system according to the invention.

As shown in FIG. 5, according to one embodiment of a respiratory gas delivery system according to the invention, the gas delivery apparatus consists of a gas blender (GB) 46, a simulated sequential gas delivery circuit (SSGDC) 200 optionally comprising a gas conduit 100 and a patient airway interface optionally in the form of mask 101 (alternatives include an endotracheal tube), one or more gas analyzers (GA), a flow sensor (FS) 40, a computer (CPU) 44 (optionally a microprocessor), an input device (ID) 102, and a display (DX) 103. The gas blender 46 optionally contains three rapid flow controllers (not shown) which are capable of delivering accurate mixes of three source gases 104 (SG1, SG2, SG3) to the circuit 200. The gases are delivered to the circuit via a gas delivery tube connecting the outlet of the gas blender 105 to the inlet 106 of the simulated sequential gas delivery circuit 200 which comprises or consists of a gas conduit 100 operatively connected to the flow sensor 40, gas analyzer(s) 42 and patient airway interface. The gas analyzer(s) 42 measures the partial pressures of gases at the airway throughout the breath. The analyzer(s) samples gas for analysis proximal to the subject's airway via a sampling catheter (not shown). A small pump (not shown) is used to draw gases from the subject's airway through the gas analyzers. Optionally, a pressure transducer 107 is used for measurement of the breath period (BP) and end-tidal detection, and also connected by a sampling catheter proximal to the subject's airway. The gas analyzers 42, flow sensor 40 and pressure transducer 107 communicate with the computer 44 via analog or digital electrical signals. The computer 44 optionally runs a software implementation of a simulation algorithm and demands the required mixtures from the blender via analog or digital electrical signals. The operator optionally enters reference breathing circuit parameters, for example the composition and flow rate into an inspiratory gas reservoir of a simulated reference SGD circuit 200 and any subject parameters. The display 103 optionally displays data/fields for inputs and outputs with respect to fixed or alterable input parameters and fixed or variable output parameters.

The respiratory gas delivery system according to the invention may be directed to supplant, in whole or part, a reference breathing circuit in the form of an SGD circuit 500 similar to the Hi-Ox 80. As seen in FIG. 3, an inspiratory limb at the 202 reference circuit 500 comprises a first gas inlet 234. Inlet 234 fills a gas reservoir 200 in the form of an inspiratory gas reservoir. A one way inspiratory valve 230 enables, for example a spontaneously breathing subject, to draw on gas in the inspiratory gas reservoir 200, so that gas enters a bifurcated portion of the circuit (optionally a y-piece) leading to the patient. The patient exhales through one-way expiratory valve 228. When the inspiratory gas reservoir 200 is depleted, valve 226 which opens at a higher pressure than one-way valve 230 responds to the increase in negative pressure, enabling a subject to draw on a second expiratory gas reservoir 220. The subject's expired air is collected in the second reservoir 220 and the inlet side 224 of the valve 226 is connected to reservoir 220. Therefore, this circuit is similar to the Hi-Ox 80 except that upon depletion of the first gas reservoir 200, the subject draws the remainder of the inspiratory cycle from the reservoir 220 containing previously expired gas as opposed to air.

This circuit may be simulated by the invention in the same way as the Hi-Ox 80 except that upon depletion of the virtual reservoir, instead of air, the microprocessor signals the gas delivery device to deliver gas with a fractional concentration of at least one gas e.g. oxygen and carbon dioxide equal to that in the gas expired in the previous breath. Optionally, the oxygen content of the gas expired in the previous breath is analyzed with an oxygen analyzer and carbon dioxide analyzer whose output is read by a microprocessor.

According to one embodiment, a virtual circuit simulates any breathing circuit, or part thereof, which operates to vary the composition and/or pattern of flow of the gas inspired by the subject by:

1. Developing a mathematical or algorithmic formulation of the behavior of the circuit, and in real-time:
2. Obtaining the inputs required to use the mathematical or algorithmic formulation to compute the composition and/or pattern of flow of the gas that would be delivered by the circuit
3. Compute the composition and/or pattern of flow of the gas that would be delivered by the circuit using the mathematical or algorithmic formulation
4. Direct an apparatus capable of controlling the composition and/or pattern of flow of inspired gas to deliver gas of a composition and/or pattern of flow equal to that the gas that would be delivered by the circuit as determined using the obtained inputs and mathematical formulation.

For example simulating SGD to vary composition only:
1. Develop mathematical formulation

```
BagVol = BagVol + G1Flow;
If(Insp)
    if(Bag=1)
        BagVol = BagVol − InspFlow;
    If(BagVol == 0)
        Bag = 2;
    If(Bag=1)
        Composition = G1Composition
    If(Bag=2)
        Composition = Last PetCO2 or TargetPetCO2
If(Exp)
    Bag =1;
```

2. Obtain inputs
From the formulation, it is obvious that the required inputs are G1Flow (input by user), G1Composition (input by user). Last PetCO2 (CO2 sensor), InspFlow (Flow sensors)
3. Use the algorithm in 1 and the inputs in 2 to compute composition
4. Direct the real-time gas-blender to deliver composition
Example: Simulating a ventilator with a mechanical pop-off valve. In this case, the ventilator will deliver some desired insp flow to the subject, and if the airway pressure exceeds the mechanical pop-off, all the delivered flow is vented and subject gets 0 flow. This can easily be simulated with a pressure sensor and control of the blower.
1. Develop mathematical formulation of behavior

```
if(Airway Pressure < PressureLimit)
    BlowerFlow = Desired Insp Flow
else
    BlowerFlow = 0
```

2. Obtain inputs
From the formulation, it is obvious that the required inputs are Desired Insp Flow (ventilator setting), Airway-Pressure (pressure sensor), PressureLimit (input by user=mechanical pop-off limit).
3. Use the algorithm in 1 and the inputs in 2 to compute BlowerFlow
4. Direct the blower to deliver BlowerFlow
Theoretically the invention can be applied to any circuit, but preferably the simulated circuit is advantageous in at least one of the following ways: less expensive, more robust, more efficient, etc. (see above) that the original circuit. In the case of SGD, this is certain.

EXAMPLE 1

In one embodiment the respiratory gas delivery system is programed to obtain the inputs related to the volume, rate of fill and depletion of an inspiratory reservoir, inspiration v. expiration, concentration of gas in inspiratory reservoir, concentration of gas in expiratory reservoir, which bag is being accessed, outputs including signaling the gas delivery device to turnoff during expiration, switch concentrations when the inspiratory reservoir is depleted switch to inspiratory reservoir concentration when inspiration is over etc. as further exemplified below:

```
// Variables
numeric inspiratory_flow;   // inspiratory flow in ml/min
numeric g1_bag_volume;      // Volume in the g1 bag in ml
numeric g1_bag_flow;        // Fill rate of the g1 bag in ml/min
numeric last_time;          // Last time the main loop was
                            // executed in ms
```

-continued

```
numeric delta_t;              // Time elapsed since last execution
                              // of the main loop in ms
numeric desired_conc_x;       // Concentration of gas x to be delivered
                              // to the subject for inspiration
numeric conc_x_g1;            // Concentration of gas x in the g1 bag
numeric conc_x_g2;            // Concentration of gas x in the g2 bag
boolean inspiration;          // Indicates inspiration or expiration
                              // Inspiration = true, Expiration = false
boolean is_bag_1;             // Indicates bag being inspired from
                              // Inspiring from g1 bag = true,
                              otherwise = false
// Main loop
do(forever)
{
    // Determine amount of time that has elapsed in ms
    // get_time( ) is a function that returns time
    // with ms resolution
    delta_t = get_time( ) - last_time;
    last_time = get time( );
    // Determine instantaneous flow in ml/min
    // read_inspiratory_flow_sensor( ) returns the
    // latest flow measurement in ml/min
    inspiratory_flow = read_inspiratory_flow_sensor( );
    // Determine bag parameters:
    //- Fill rate of g1 bag
    // - Concentration of gas x in g1 bag
    // - Concentration of gas x in g2 bag
    // These parameters may be sent to the device running
    // this code by the operator or another device. For example,
    // this code may be run on a micro-processor and these
    // parameters sent to this micro-processor by a PC.
    // The function read_in( ) is assumed to populate the values
    // of these parameters.
    read_in(g1_bag_flow,conc_x_g1, conc_x_g1);
    // Determine if inspiration or expiration:
    // Switch to inspiration if currently expiring and
    // inspiratory flow exceeds a threshold. Switch
    // to expiration if currently inspiring and flow
    // drops below a threshold. In this case, the threshold
    // is 500 ml/min but could be set depending on the size of
    // the subject and the resolution/noise of the flow sensor.
    if(is_inspiration = false AND inspiratory_flow > 500 ml/min)
    {
        is_inspiration = true;
    }
    else if(is_inspiration = true AND inspiratory_flow < 500 ml/min)
    {
        is_inspiration = false;
    }
    // Increase the volume in the g1 bag by the gas
    // flow that has accumulated since the last time
    // the main loop was executed
    // 60000 converts ml/min to ml/ms
    g1_bag_volume += g1_bag_flow * delta_t * 60000;
    // Inspiring from the g1 bag
    if(is_inspiration = true AND is_bag_1 = true)
    {
        // Decrease the volume in the g1 bag by the
        // gas that has been inspired since the last
        // time the main loop was executed
        // 60000 converts ml/min to ml/ms
        g1_bag_volume = inspiratory_flow * delta_t * 60000;
        // Signal the gas delivery device to
        // deliver the concentration of gas x
        // in the g1 bag
        desired_conc_x = conc_x_g1;
        // If the g1 bag is empty switch to the g2 bag
        if(g1_bag_volume <= 0)
        {
            bag = 2;
        }
    }
    // Inspiring from the g2 bag
    else if(is_inspiration = true AND is_bag_1 = false)
    {
        // Signal the gas delivery device to
        // deliver the concentration of gas x
        // in the g2 bag
        desired_conc_x = conc_x_g2;
    }
    // Expiration
    else
    {
        // Signal the gas delivery device to
        // turn off during expiration
        desired_conc_x = 0;
        // When the inspiration is over, switch
        // bag to the g1 bag for the next breath
        is_bag_1 =true;
    }
    // Signal the gas delivery device to
    // deliver the desired concentration
    // of gas x:
    // set_inspired_concentration_of_gas_x( )
    // is a function which accepts the desired
    // concentratton of gas x, and signals
    // the gas delivery device to deliver the
    // desired concentration
    set_inspired_concentration_of_gas_x(desired_conc_x);
} // End of main loop
```

The invention claimed is:

1. A respiratory gas delivery system adapted to deliver an inspiratory gas of variable composition to a subject via a patient airway interface of a breathing circuit, the respiratory gas delivery system comprising:
   a gas delivery apparatus operatively connected to a processor;
   a flow sensor adapted to monitor in real time the rate of inspiration of the inspiratory gas by the subject via the patient airway interface; and
   a gas analyzer adapted to determine the composition of one or more gases exhaled;
   wherein, for a plurality of respective inspiratory cycles and a plurality of time points over the course of a respective inspiratory cycle, the processor is configured to:
   (a) use output from the flow sensor to monitor the cumulative volume of gas inspired by the subject in the respective inspiratory cycle at any given time point;
   (b) use output from the gas analyzer to determine the composition of the one or more gases exhaled;
   (c) determine a desired composition of the gas inspired in the respective inspiratory cycle, the desired composition including a composition selected from a first composition of at least one constituent gas X selected for delivery for a first portion of a respective inspiratory cycle and at least one alternate nth composition of the at least one constituent gas X selected for delivery during the course of a second portion of the respective inspiratory cycle, the first portion of the respective inspiratory cycle corresponding to a threshold cumulative volume of the first composition for the respective inspiratory cycle, the threshold cumulative volume being less than the subject's tidal volume minus anatomic dead space volume, such that the entirety of the threshold cumulative volume is destined to enter the subject's alveolar space via the patient airway interface, and the at least one alternate nth composition corresponding with the composition of the one or more gases gas exhaled; and
   (d) generate a control signal effective to signal the gas delivery apparatus to deliver the first composition in the first part of the respective inspiratory cycle and then the at least one alternate nth composition if the threshold cumulative volume for the respective inspiratory cycle has been reached during the course of the respective inspiratory cycle.

2. A respiratory gas delivery system as claimed in claim 1, wherein volumes of a first component gas incrementally inspired at the time points, in the respective inspiratory cycle are accumulated in a processor memory, wherein the processor is adapted to monitor inspiration of the threshold cumulative volume of the first composition.

3. A non-transitory computer readable medium comprising instructions executable by a processor to:
use output from a flow sensor of a gas delivery apparatus to monitor a volume of gas inspired by a subject in an inspiratory cycle;
use output from a gas analyzer of the gas delivery apparatus to determine the composition of one or more gases exhaled;
determine a composition of a first gas to be inhaled over a first portion of the inspiratory cycle, the first gas including at least a first constituent gas and the volume of the first gas corresponding to a volume that is less than a tidal volume of the subject minus anatomic dead space volume such that the volume of the first gas is destined to enter the subject's alveolar space; and
determine a composition of a second gas to be inhaled over a second portion of the inspiratory cycle, the second gas including at least a second constituent gas, the composition of the second gas corresponding to the composition of the one or more gases exhaled.

4. The non-transitory computer readable medium of claim 3 wherein the first gas comprises at least one therapeutic gas.

5. The non-transitory computer readable medium of claim 3 wherein the composition of the second gas is neutral with respect to the subject's arterial blood.

6. The non-transitory computer readable medium of claim 3 wherein the instructions are further executable to determine the composition of the first gas such that a target volume of at least the first constituent gas is delivered over a series of inspiratory cycles.

7. The non-transitory computer readable medium of claim 3 wherein the instructions are further executable to correspond the composition of the second gas with the composition of one or more gases exhaled at the end of exhalation.

8. The non-transitory computer readable medium of claim 3 wherein the instructions are further executable to determine the volume and composition of the first gas necessary to attain a target end tidal concentration of the first constituent gas.

9. The non-transitory computer readable medium of claim 3 wherein the instructions are further executable to compose the first and second gas using a gas blender.

10. The non-transitory computer readable medium of claim 3 wherein the instructions are further executable to control the tidal volume of the subject using a ventilator.

* * * * *